United States Patent
Den Hartog et al.

(10) Patent No.: US 6,335,326 B1
(45) Date of Patent: Jan. 1, 2002

(54) BENZISOXAZOLE DERIVATIVES HAVING D4-ANTAGONISTIC ACTIVITY

(75) Inventors: Jacobus A. J. Den Hartog; Gerben M. Visser; Bartholomeus J. Van Steen; Martinus T. M. Tulp; Eric Ronken; Cornelis G. Kruse; Josephus H. M. Lange, all of Weesp (NL)

(73) Assignee: Duphar International Research B.V. (NL)

( * ) Notice: Subject to any disclaimer, the term of this patent is extended or adjusted under 35 U.S.C. 154(b) by 0 days.

(21) Appl. No.: 09/601,795

(22) PCT Filed: Feb. 5, 1999

(86) PCT No.: PCT/EP99/00852

§ 371 Date: Oct. 23, 2000

§ 102(e) Date: Oct. 23, 2000

(87) PCT Pub. No.: WO99/40067

PCT Pub. Date: Aug. 12, 1999

(30) Foreign Application Priority Data

Feb. 9, 1998 (EP) .............................. 98200400

(51) Int. Cl.[7] .................. A01N 43/46; A01N 43/40
(52) U.S. Cl. ................. 514/212; 514/321; 514/323; 546/198; 546/201; 540/524
(58) Field of Search ................ 546/201, 198; 540/524; 514/323, 321, 212

(56) References Cited

U.S. PATENT DOCUMENTS 4,352,811 A  10/1982  Strupzewski et al. ....... 546/198

FOREIGN PATENT DOCUMENTS

EP       0 602 242 A1  6/1994  .................. 546/198
WO       WO 99/40067   8/1999  .................. 546/198

*Primary Examiner*—Alan L. Rotman
*Assistant Examiner*—Raymond Covington
(74) *Attorney, Agent, or Firm*—Finnegan, Henderson, Farabow, Garrrett and Dunner, L.L.P.

(57) ABSTRACT

The present invention relates to a group of novel benzisoxazole derivatives which are potent and selective antagonists of the dopamine D4-receptor. The compounds have general formula (I) wherein $(R_1)_n$ represents 0, 1, or 2 substituents, which can be the same or different, from the group $C_{1-3}$-alkyl or alkoxy, halogen, trifluoromethyl, nitro, amino mono- or dialkyl $(C_{1-2})$-amino, sulfonyl-$(C_{1-3})$alkyl or -alkoxy, sulfonyl trifluoromethyl, sulfonyl amino, and sulfonyl mono- or dialkyl $(C_{1-2})$-amino, X is O, S, NH or $NCH_3$, Y represents $CH_2$, or $(CH_2)_2$, $(R_2)_m$ represents 0, 1, or 2 substituents, which can be the same or different, from the group methyl and ethyl, or $(R_2)_m$ is a methylene bridge or ethylene bridge, A is a group —$CH_2$—$(CRH)_p$— wherein R is hydrogen or methyl and p is 0 or 1, and B represents 2- or 3-indolyl or 2-benzimidazolyl, which groups may be substituted at carbon with 1 or 2 substituents from the group $C_{1-3}$-alkyl or alkoxy, halogen, trifluoromethyl, nitro, amino, mono- or dialkyl $(C_{1-2})$amino, sulfonyl-$(C_{1-3})$alkyl or -alkoxy, sulfonyl trifluoromethyl, sulfonyl amino, and sulfonyl mono- or dialkyl $(C_{1-2})$-amino.

(I)

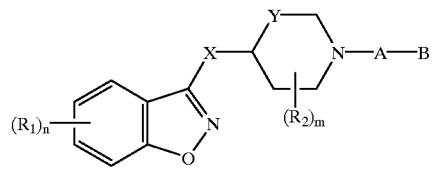

13 Claims, No Drawings

BENZISOXAZOLE DERIVATIVES HAVING D4-ANTAGONISTIC ACTIVITY

The present invention relates to a group of novel benzisoxazole derivatives, to a method for the preparation of these compounds, and to pharmaceutical compositions containing one or more of these compounds as an active component.

It has surprisingly been found that the compounds and salts thereof of the formula (I)

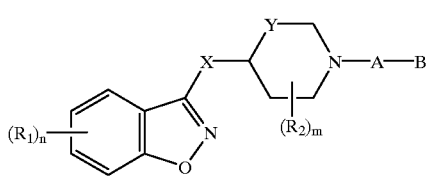

wherein
($R_1$), represents 0, 1 or 2 substituents, which can be the same or different, from the group $C_{1-3}$-alkyl or alkoxy, halogen, trifluoromethyl, nitro, amino, mono- or dialkyl ($C_{1-2}$)-amino, sulfonyl-($C_{1-3}$)alkyl or -alkoxy, sulfonyl trifluoromethyl, sulfonyl amino, and sulfonyl mono- or dialkyl ($C_{1-2}$)-amino, X is O, S, NH or $NCH_3$, Y represents $CH_2$ or $(CH_2)_2$ $(R_2)_m$ represents 0, 1, or 2 substituents, which can be the same or different, from the group methyl and ethyl, or $(R_2)_m$ is a methylene bridge or ethylene bridge, A is a group —$CH_2$—$(CRH)_p$— wherein R is hydrogen or methyl and p is 0 or 1, and B represents 2- or 3-indolyl or 2-benzimidazolyl, which groups may be substituted at carbon with 1 or 2 substituents from the group $C_{1-3}$-alkyl or alkoxy, halogen, trifluoromethyl, nitro, amino, mono- or dialkyl ($C_{1-2}$)amino, sulfonyl-($C_{1-3}$)alkyl or -alkoxy, sulfonyl trifluoromethyl, sulfonyl amino, and sulfonyl mono- or dialkyl ($C_{1-2}$)amino, are potent and selective antagonists of the dopamine D4-receptor.

Compounds having formula (I) wherein A is the group $CH_2$, Y is $CH_2$, X is O, NH or $NCH_3$ and m and n are 0, and B has the above meaning, and salts thereof are preferred.

Due to the potent and selective D4 antagonistic activity the compounds according to the invention are suitable for use in the treatment of psychiatric disorders such as psychosis, anxiety, depression, attention deficits and memory disorders, neurological disorders such as Parkinson's disease and ischaemia and other CNS-diseases involving dopaminergic neurotransmission.

The affinity of the compounds of the invention for dopamine D4 receptors was determined using CHO-K1 cells which are stably transfected to express the human recombinant dopamine receptor, D4.2 subtype (Van Tol et al, Nature 350, 610, 1991) and using [3H]-Spiperone as the ligand. After incubation of a freshly prepared cellmembrane preparation with the [3H]-ligand, with or without addition of compounds of the invention, separation of bound and free ligand was performed by filtration over glassfiberfilters (Research Biochemicals International protocol, Catalog No. D-177). Radioactivity on the filter was measured by liquid scintillation counting. Results are expressed as IC50 values and transformed into inhibitory constants (Ki).

The dopamine D4 antagonistic activity of compounds of the invention was determined by functional studies using CHO-K1 cells stably expressing the human dopamine D4.4 receptor (Van Tol et al, Nature 358, 149, 1992).These cells were fitted with a construct encoding a truncated form of alkaline phosphatase, causing it to get secreted by the cells. Expression of this secretable alkaline phosphatase (SeAP) is under direct control of cellular cyclic AMP (Berger et al, Gene, 66, 1, 1988). SeAP measurements were done with p-nitrophenylphosphate (pNPP) as the substrate using colorimetric readout at 450 nm. Dopamine D4 antagonist activity was determined by co-incubation of cells with prostaglandin PGE1 (1 $\mu$M) and quinpirole (1 $\mu$M), with or without addition of compounds of the invention, for receptor-mediated stimulation of adenylate cyclase and for maximal dopamine D4 receptor-mediated suppression, respectively. The antagonistic effect of compounds of the invention against agonist dependant attenuation of dopamine D4 receptor mediated SeAP formation was quantified, yielding estimates of intrinsic activity and potency (pA2 values). Clozapine and spiperone were used as reference dopamine antagonists.

Absence of dopamine D4 agonistic activity was confirmed using the same assay, but leaving out the standard dopamine D4 agonist quinpirole, by determination of the concentration-dependant attenuation of the dopamine D4 receptor mediated SeAP formation by compounds of the invention.

Dopamine D4 antagonist properties and absence of dopamine D4 agonist properties of selected compounds of the invention were further confirmed using radioactive measurements of cAMP formation according to Salomon et al. (Anal Biochem, 58, 541, 1974) as modified by Weiss et al. (J Neurochem 45, 869, 1985).

The selectivity of the compounds of the invention with regard to the dopamine D2 receptor, was determined by measuring the affinity for dopamine D2 receptors using rat brain homogenates and [3H]-Spiperone as the ligand (Leysen et al, Biochem Pharmacol 27, 307, 1978). After incubation of a freshly prepared cellmembrane preparation with the [3H]-ligand, with or without addition of compounds of the invention, separation of bound and free ligand was performed by filtration over glassfiberfilters. Radioactivity on the filter was measured by liquid scintillation counting. Results are expressed as IC50 values and transformed into inhibitory constants (Ki).

The dopamine D2 (ant)agonistic activity of compounds of the invention was determined by functional studies based on radioactive measurements of cAMP formation according to Salomon et al. (Anal Biochem, 58, 541, 1974), as modified by Weiss et al. (J Neurochem, 45, 869, 1985), using CHO cells, stably expressing human dopamine D2L receptors (Grandy et al, Proc Natl Acad Sci USA, 86, 9762, 1989). Suitable acids with which the compounds can form pharmaceutically acceptable acid addition salts are for example hydrochloric acid, sulphuric acid, phosphoric acid, nitric acid, and organic acids such as citric acid, fumaric acid, maleic acid, tartaric acid, acetic acid, benzoic acid, p-toluene sulphonic acid, methane sulphonic acid and naphthalene sulphonic acid.

The compounds of the invention can be brought into forms suitable for administration by means of usual processes using auxiliary substances and/or liquid or solid carrier materials.

The compounds of the invention having formula (I) can be obtained according to methods known for the synthesis of structurally related compounds.

A suitable synthesis for the compounds according to the present invention is the following:

Step 1

Reaction of a compound having formula (II)

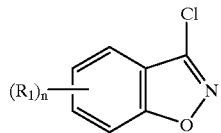
(II)

with a compound of the formula (III)

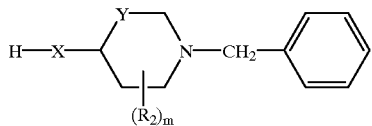
(III)

This reaction is carried out in a polar aprotic solvent such as dimethylformamide in the presence of an equivalent amount of a base such as sodiumhydride at 20–120° C. The protecting benzyl group is then removed from the obtained product.

Step 2

When B is the group 2- or 3-indolyl, the thus obtained deprotected compound having formula (IV)

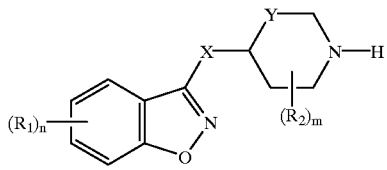
(IV)

is reacted with an optionally substituted 2- or 3-indolyl carboxylic acid derivative of the formula B-A'—COOH, wherein A' is the group -(CRH)$_p$—, wherein R is hydrogen or methyl and p has the value 0 or 1. This reaction is carried out in the presence of an equivalent amount of 1,1'-carbonyldiimidazole in an aprotic solvent such as tetrahydrofuran.

Step 3

The keto group in the obtained compound of the formula (V)

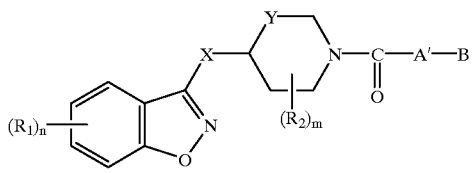
(V)

is reduced to CH$_2$ in a manner known per se, e.g. by means of an excess of sodium borohydride in the presence of acetic acid in a solvent such as dimethoxyethane under an atmosphere of nitrogen to give the desired compound having formula (I).

To prepare a compound having formula (I) wherein B is the group 2-benzimidazolyl, the compound having formula (IV) is reacted with an optionally substituted 2-halomethyl benzimidazole derivative of the formula B—A—Z, wherein A has the above meaning and Z is Cl or Br. This reaction is carried out in the presence of a base such as triethylamine in a polar aprotic solvent such as acetonitrile at 20–80° C.

The preparation of the compounds is illustrated in the following examples.

EXAMPLE I 3-(4-Oxo-[1-(2-methylindolyl)piperidino])-benzisoxazole.hydrochloride

Part A: A quantity of 19.1 g (100 mmol) of commercially available, dry 4-hydroxy-1-benzyl-piperidine was dissolved in dimethylformamide (150 ml) and 6.4 g (55% quality; 100 mmol) sodiumhydride was added. After stirring at 80° C. for 1 hr the mixture was cooled to room temperature and 15.4 g (100 mmol) of 3-chloro-benzisoxazole ((H. Boshagen, Chem. Ber. 1967, 100, pg 3326) was added in portions. After stirring at room temperature for 1 hr and at 80° C. for 3 hr, the mixture was cooled to room temperature and water (300 ml) was added. The solution was extracted with dichloromethane (three times 150 ml), the organic layer was subsequently washed with water (three times 40 ml), dried over magnesium sulphate and concentrated in vacuo. The product was purified applying flash-chromatography over silica gel using dichloromethane/methanol 99:1 as the eluent. After concentration in vacuo a total of 25.6 g of 3-(4-oxo-1-benzyl-piperidino)-benzisoxazole was obtained (83% yield)

Part B: To a solution of 25.6 g (83 mmol) of 3-(4-oxo-1-benzyl-piperidino)-benzisoxazole in 1,2-dichloroethane (200 ml) a solution of 1-chloroethyl chloroformate (13.6 ml, 125 mmol, 1.5 equivalent) was added dropwise under ice cooling. The mixture was stirred at 0° C. for ½ hr, at room temperature for 1 hr, refluxed for 2 hrs and subsequently cooled to room temperature. After concentration in vacuo, methanol (200 ml) was added and the resulting mixture was refluxed for 2 hrs. The precipitate obtained after subsequent cooling to 0° C. was collected by filtration, washed with petroleum-ether (40–60) and dried in vacuo. In this way 14.5 g of 3-(4-oxo-piperidino)-benzisoxazole.hydrochloride was obtained as a pink solid (69% yield).

Part C: A quantity of 9.7 g (60 mmol) of commercially available indole-2-carboxylic acid and 9.8 g (60 mmol) of commercially available 1,1'-carbonyldiimidazole were dissolved in dry tetrahydrofuran (300 ml), the reaction mixture was refluxed under nitrogen for 1 hr and subsequently cooled in ice.

Meanwhile the obtained 14.5 g (57 mmol) of 3-(4-oxo-piperidino)-benzisoxazole.hydrochloride was dissolved in a sodium hydroxide solution in water (2N, 200 ml) and extracted with dichloromethane (three times 100 ml). The combined organic layers were dried over sodium sulphate, concentrated in vacuo and dissolved in dry tetrahydrofuran (70 ml). The obtained solution of 3-(4-oxo-peperidino)-benzisoxazole was added to the solution of activated indole-2-carboxylic acid and the resulting reaction mixture was refluxed for 2 hrs. After concentration in vacuo, water (200 ml) was added. After washing with dichloromethane (three times 70 ml) the combined organic layers were washed with water (three times 40 ml), dried over sodium sulphate and concentrated in vacuo. The resulting yellow solid was suspended under stirring in diisopropylether (300 ml). After 40 hrs the precipitate was collected by filtration, washed with diisopropylether (two times 150 ml) and dried in vacuo. A quantity of 18.4 g of 3-(4-oxo-[1-(2-carboxy-indolyl)
piperidino])benzisoxazole was obtained as a white solid
(89% yield).

Part D: To a solution of 18.4 g (50 mmol) of 3-(4-oxo-
[1-(2-carboxy-indolyl)piperidino])benzisoxazole and 9.5 g
(250 mmol, 5 equivalent) of sodium borohydride in dry
1,1-dimethoxyethane (400 ml) under nitrogen, a solution of
14.3 ml (250 mmol) acetic acid in dry 1,2dimethoxyethane
(100 ml) was added dropwise in ½ hr. The mixture was
refluxed for 1 hr. After cooling of the reaction mixture in ice,
subsequent dropwise addition was carried out of: 1). a
mixture of water (9.5 ml) and 1,2-dimethoxyethane (100
ml), 2). water (90 ml) and 3). a solution of sodiumhydroxide
in water (2N, 15 ml). The reaction mixture was refluxed for
2 hrs. The precipitate obtained after cooling to room temperature was removed by filtration. To the filtrate water (300
ml) and ethylacetate (50 ml) were added, the water layer was
further extracted with ethylacetate (two times 150 ml) and
the combined organic layers were washed with water (three
times 70 ml), dried over sodium sulphate and concentrated
in vacuo. The residual yellow oil was dissolved in absolute
ethanol (200 ml), heated to 70° C. and a solution of 1.83 g
hydrochloride in absolute ethanol (15 ml) was
added. After stirring for ½ hr at 70° C., subsequent cooling
and stirring at room temperature for 2 hrs, the resulting
precipitate was collected by filtration, washed with absolute
ethanol (two times 25 ml) and dried in vacuo. In this way
15.2 g of 3-(4-oxo-[1-(2-methylindolyl)piperidino])-
benzisoxazole.hydrochloride was obtained as a white solid
(79% yield) with a melting point of 225° C.

In an analogous manner the compounds having formula
(I) listed below have been prepared:

TABLE

| Example | $(R_1)_n$ | X | Y | $(R_2)_m$ | A | B | Salt |
|---|---|---|---|---|---|---|---|
| II | H | $NCH_3$ | $CH_2$ | H | $CH_2$ | 2-indolyl | base |
| III | H | NH | $CH_2$ | H | $CH_2$ | 2-indolyl | fumarate |
| IV | H | $NCH_3$ | $CH_2$ | H | $CH_2$ | 2-benzimidazolyl | HCl |
| V | H | $NCH_3$ | $CH_2$ | H | $CH_2$ | 4-Cl-2-indolyl | base |
| VI | H | $NCH_3$ | $CH_2$ | H | $CH_2$ | 5-F-2-indolyl | base |
| VII | H | $NCH_3$ | $CH_2$ | H | $CH_2$ | 3-indolyl | fumarate |

What is claimed is:
1. A compound of formula (I) or a salt thereof

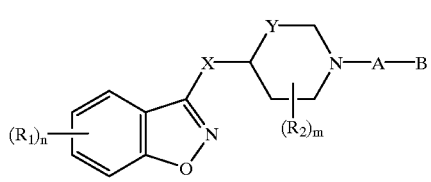

(I)

wherein
$(R_1)_n$ represents 0, 1 or 2 substituents, which substituents
can be the same or different, and are chosen from
$C_{1-3}$-alkyl, $C_{1-3}$ alkoxy, halogen, trifluoromethyl, nitro,
amino, monoalkyl-$(C_{1-2})$-amino, dialkyl $(C_{1-2})$-amino,
sulfonyl-$(C_{1-3})$alkyl, sulfonyl-$(C_{1-3})$alkoxy, sufonyl
trifluoromethyl, sulfonyl amino, sulfonyl monoalkyl-
$(C_{1-2})$-amino and sulfonyl dialkyl $(C_{1-2})$-amino groups;
X is O, S, NH or $NCH_3$;
Y is $CH_2$ or $(CH_2)_2$;

$(R_2)_m$ represents 0, 1, or 2 substituents, which substituents
can be the same or different, and are chosen from
methyl and ethyl groups, or $(R_2)_m$ is a methylene bridge
or ethylene bridge;

A is a group —$CH_2$—$(CRH)_p$— wherein R is hydrogen or
methyl and p is 0 or 1; and B is a 2- or 3-indolyl or a 2-benzimidazolyl group, which
group may be substituted at each carbon with 1 or 2
substituents chosen from $C_{1-3}$-alkyl, $C_{1-3}$-alkoxy,
halogen, trifluoromethyl, nitro, amino, monoalkyl-
$(C_{1-2})$ amino, dialkyl $(C_{1-2})$amino, sulfonyl-$(C_{1-3})$
alkyl, sulfonyl-$(C_{1-3})$alkoxy, sulfonyl trifluoromethyl,
sulfonyl amino, sulfonyl monoalkyl-$(C_{1-2})$amino and
sulfonyl dialkyl $(C_{1-2})$-amino groups.

2. The compound according to claim 1, wherein A is $CH_2$,
Y is $CH_2$, X is O, NH or $NCH_3$, and m and n are 0.

3. A method for preparing a compound of formula (I) or
salt thereof according to claim 1, said method comprising
a) reacting a compound of a formula (IV):

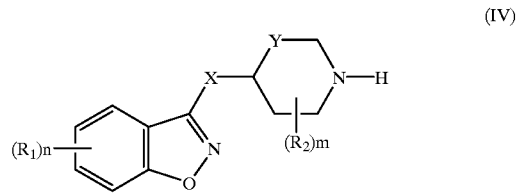

(IV)

wherein $(R_1)_n$, x, y, and $(R_2)_m$ are defined as in claim
1, with a substituted or unsubstituted 2- or 3-indolyl
carboxylic acid derivative of the formula B-A'—
COOH, wherein A' is a —$(CRH)p$- group, in which
R is hydrogen or methyl, and p is 0 or 1, and B is
defined as in claim 1, to obtain a compound of a
formula (V):

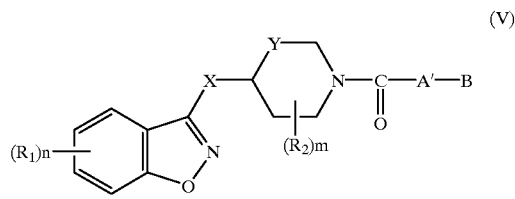

(V)

and reducing the keto group of said compound of
formula (V); or b) reacting a compound of formula (IV) as defined above
with a substituted 2-halomethyl benzimidazole derivative of the formula B-A-Z, wherein B is
2-benzimidazolyl, A is a —$CH_2$—$(CRH)_p$— group,
wherein R is hydrogen or methyl and p is 0 or 1, and
Z is chloro or bromo.

4. A pharmaceutical composition, said composition comprising at least one compound of formula (I) according to claim 1, or a salt thereof, as an active component.

5. The composition according to claim 4, wherein said active component is present in an amount effective for treatment of at least one CNS disease involving dopaminergic neurotransmission.

6. The composition according to claim 4, wherein said composition further comprises a liquid or solid carrier material.

7. A method for preparing a pharmaceutical composition, said method comprising including in said composition a compound of formula (I) according to claim 1, or a salt thereof, as an active component.

8. The method according to claim 7, wherein said active component is present in an amount effective for treatment of at least one CNS disease involving dopaminergic neurotransmission.

9. The method according to claim 7, wherein said composition further comprises a liquid or solid carrier material.

10. A method for treating a psychiatric disorder, said method comprising administering to a host in need of said treatment an effective amount of a compound of formula (I) according to claim 1, or a salt thereof.

11. The method according to claim 10, where said psychiatric disorder comprises at least one disorder chosen from psychosis, anxiety, depression, attention deficit disorder and memory disorders.

12. A method for treating a neurological disorder, said method comprising administering to a host in need of said treatment an effective amount of a compound of formula (I) according to claim 1, or a salt thereof.

13. The method according to claim 12, where said neurological disorder comprises at least one disorder chosen from Parkinson's disease and ischaemia.

* * * * *